United States Patent
Kaga et al.

(10) Patent No.: US 7,804,406 B2
(45) Date of Patent: Sep. 28, 2010

(54) QUALITY CONTROL SYSTEM OF CONCRETE AND CEMENT PRODUCTS USING WIRELESS IC TAG

(75) Inventors: Kikuo Kaga, Tokyo (JP); Shigeo Ashizawa, Tokyo (JP); Yasuo Kano, Tokyo (JP)

(73) Assignee: Mitomo Corporation, Kanagawa (JP)

( * ) Notice: Subject to any disclaimer, the term of this patent is extended or adjusted under 35 U.S.C. 154(b) by 686 days.

(21) Appl. No.: 11/651,049

(22) Filed: Jan. 9, 2007

(65) Prior Publication Data

US 2008/0067228 A1 Mar. 20, 2008

(30) Foreign Application Priority Data

Sep. 11, 2006 (JP) .............................. 2006-245352

(51) Int. Cl.
*G08B 13/14* (2006.01)

(52) U.S. Cl. .............. 340/572.1; 340/572.8; 340/572.9; 340/10.3; 340/10.33; 340/10.4; 340/10.41; 324/632; 324/634; 324/636; 324/640; 324/658; 73/53.06; 73/54.03; 73/54.14; 73/61.41

(58) Field of Classification Search .............. 340/572.1, 340/572.8, 572.9, 568.1, 10.3, 10.33, 10, 340/34, 10.4, 10.41; 324/632, 640, 642, 324/643, 647, 634, 635, 639, 644, 658; 73/54.03, 73/61.41, 53.06, 54.14; 235/375; 52/20, 52/21; 264/238; 249/205

See application file for complete search history.

(56) References Cited

U.S. PATENT DOCUMENTS

| 7,551,058 | B1 * | 6/2009 | Johnson et al. | .......... 340/10.41 |
| 2005/0156707 | A1 * | 7/2005 | Kudo | ........................ 340/5.91 |

FOREIGN PATENT DOCUMENTS

| JP | 2004-043143 | 2/2004 |
| JP | 2004-109002 | * 4/2004 |
| JP | 2005-191705 | 7/2005 |
| JP | 2005-330729 | 12/2005 |
| JP | 2006-145385 | 6/2006 |

* cited by examiner

*Primary Examiner*—George A Bugg
*Assistant Examiner*—Sisay Yacob
(74) *Attorney, Agent, or Firm*—Wenderoth, Lind & Ponack, L.L.P.

(57) ABSTRACT

A quality control system of concrete and cement products is provided in which the manufacturing information on cement products of mortar or concrete can be checked at any time, the reliability is such that there is no possibility of the recorded information being lost or falsified, there is no possibility of damage in concrete, and the directivity of the sensitivity of an antenna can be broadened.

34 Claims, 2 Drawing Sheets

US 7,804,406 B2

QUALITY CONTROL SYSTEM OF CONCRETE AND CEMENT PRODUCTS USING WIRELESS IC TAG

BACKGROUND OF THE INVENTION

1. Field of the Invention

The present invention relates to a quality control to enhance the reliability of a concrete structure, more particularly, to a quality control system of concrete and cement products which can check the information during manufacture of the cement products used for the structure on the construction field easily and with high reliability.

2. Prior Art

As to civil engineering-related concrete structures and buildings, it is necessary to verify the information including concrete strength and the records of construction work during maintenance or in time of disaster including earthquakes. Said information was controlled by being recorded in writing with drawings, but there was the possibility of said writing being lost or said information being falsified. In recent years said information has been recorded in the database of computers other than in writing, but there is still a risk of loss or falsification of said information. Consequently, said conventional quality control systems of concrete were not necessarily reliable to the owners and the users of concrete structures.

In addition, a method of affixing an IC tag in which the information on distribution management including building materials to building materials or wall surfaces of buildings (e.g. Patent Document 1) and a method of laying an wireless IC tag in concrete before hardening (e.g. Patent Document 2 and 3) have been devised.

[Patent Document 1] Japanese Published Unexamined Patent Application No. 2004—Gazette No. 141483

[Patent Document 2] Japanese Published Unexamined Patent Application No. 2005—Gazette No. 330729

[Patent Document 3] Japanese Published Unexamined Patent Application No. 2006—Gazette No. 183257

However, as the above-mentioned conventional IC tag was arranged in an exposed place and needed manpower in the process from recording the information to being installed to structures, there were possibilities of the information recorded in IC tags being falsified as well as the damage or the loss of IC tags and there was also a doubt of being replaced by the falsified IC tags. If the conventional IC tags were put into concrete, there was the possibility of being damaged in the sheet-like form by considerable stress applied during kneading or casting. Furthermore, as a plane-shaped antenna was installed on the surface of the conventional tabular IC tag, a sensitivity of a directivity of an antenna for wireless contact became poorer with the peak of the orthogonal direction on the surface of the IC tag as it inclined more, and it became impossible to send or receive any data in a parallel direction to the surface of the IC tag, a narrowness of the directivity of the sensitivity of antennas was a problem.

SUMMARY OF THE INVENTION

The present invention is made to resolve the above-mentioned problems and has an object of providing a quality control system of concrete and cement products in which the information including the proportion of water to cement, cement admixture and the temperature of cement products including mortar and concrete during manufacture can be checked at any time, and in which the reliability is such that there is no possibility of the recorded information being lost or falsified or being damaged in concrete, and the directivity of the sensitivity of antennas can be broadened.

DETAILED DESCRIPTION OF THE PREFERRED EMBODIMENTS

Figure 1:
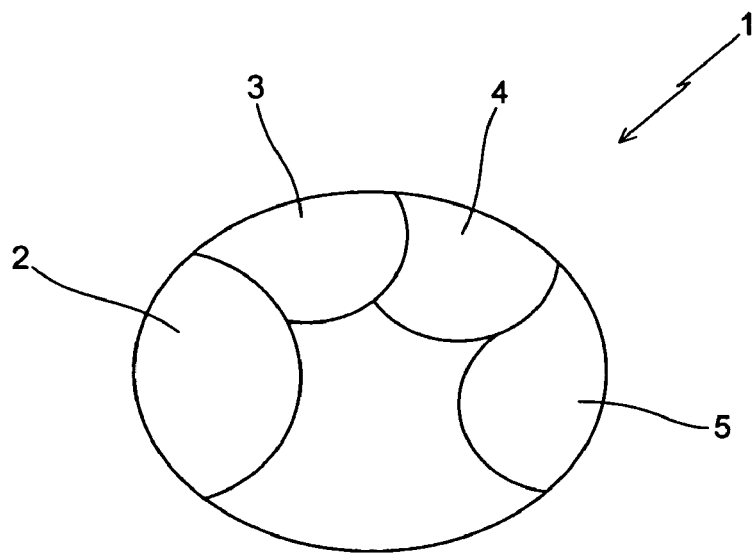
FIG. 1 is a graphical illustration of a wireless IC tag used for the present invention.
Figure 2:
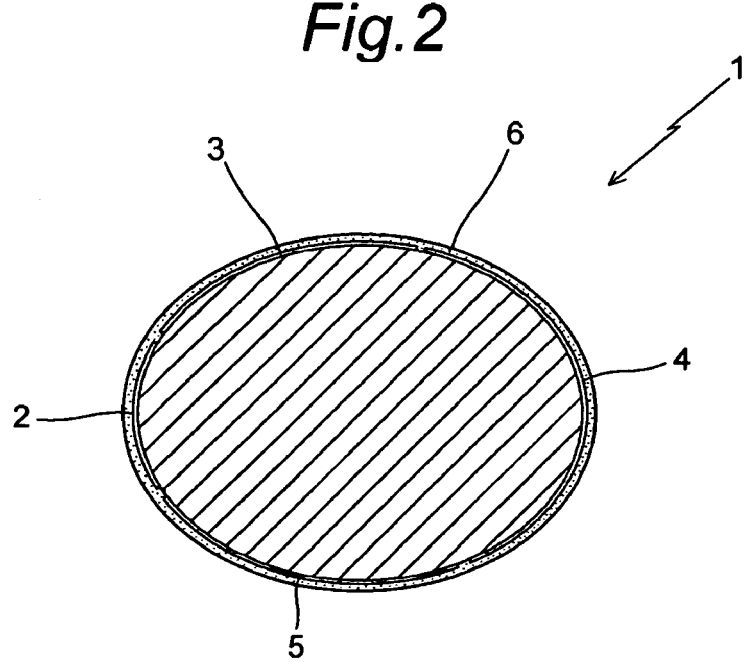
FIG. 2 is a graphical illustration showing a cross section of a wireless IC tag used for the present invention.

FIG. 1 and FIG. 2 are conceptual diagrams showing a wireless IC tag 1 used for a quality control system of concrete using the wireless IC tag of the present invention. This wireless IC tag 1 has a solid form including a sphere, an ellipsoid or a polyhedron (e.g. 32-hedron), the outer circumference is coated with glass or ceramic, by making specific gravity with the size the same as aggregate including gravels mixed together, not only the kneading of cement products can be done dispersedly without unevenness during kneading of cement products but also an applied force during kneading, an applied stress during casting and a compression force of concrete itself can be sufficiently endured. The shape of this wireless IC tag 1 is like a glass ball whose size is from approximately a few millimeters to a few dozen of millimeters.

The wireless IC tag 1 comprises a FeRAM 2 that is a nonvolatile memory using ferroelectric substances, a power section 3 which receives radio waves from outside instead of having a battery for driving built-in and generates an electrical current by resonating with this, an antenna section 4 for communicating wirelessly at a low frequency in a kilohertz band and a control section 5 to control these by being formed three-dimensionally following on a curved surface (a bended curved surface is acceptable) of the wireless IC tag 1 in a solid form, and then, as shown in FIG. 2, a coating substance 6 including glass covers the whole to protect these.

In this wireless IC tag 1, by setting a radio wave band to communicate wirelessly to low frequency of kilohertz band, the distance for the wireless IC tag 1 to be able to communicate wirelessly with an IC tag writer and an IC tag reader dramatically increases by 10 m compared with the IC tag using radio waves of the conventional megahertz band (outreach of a few meters or less). By encrypting a signal used for this wireless communication, the signal cannot be written in or read out except by the device previously set to be able to decrypt signals, so the information can be completely controlled. In addition, by forming an antenna section 4 to be a three-dimensional shape with a curved surface, it becomes easy to communicate wirelessly from every direction because of multidirectional spread of the directivity of an antenna compared with the conventional planate antenna. Furthermore, as FeRAM 2 can be written in at low voltage of DC 1.1 V, a passive type equipped with a power section 3 generating electricity by resonating with waves from outside without having a battery inside a wireless IC tag 1, and has a writing speed 5,000 times faster than EEPROM used in the conventional IC tag. Then while the number of times of EEPROM is about 100,000, that of FeRAM 2 is 12-plex and FeRAM 2 has a superior performance. As to the access to rewriting, while most conventional EEPROM and flash memory are in a block unit, FeRAM has the advantage of being in a random manner in a word unit. A control section 5 to control writing to FeRAM 2 is set not to be overwritable but to be addable in order for the information written in once not to be falsified.

Figure 3:
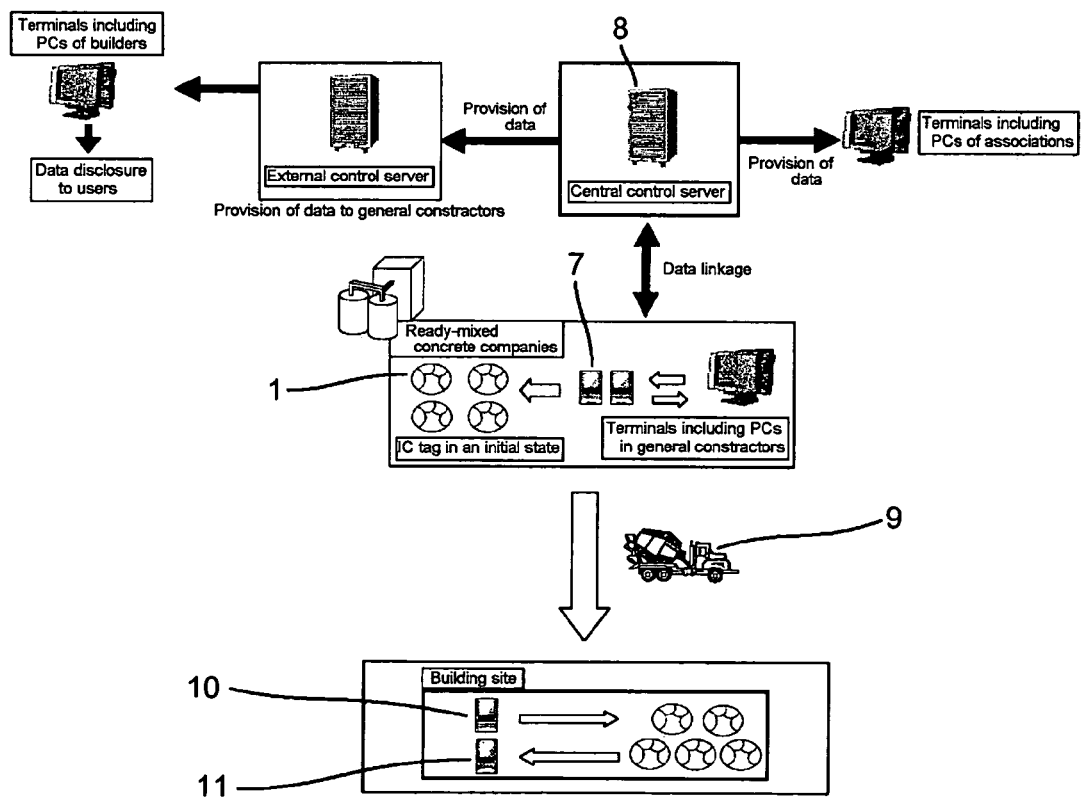
FIG. 3 is a graphical illustration of a quality control system of concrete using a wireless IC tag of the present invention.

Described below is a quality control system of concrete using a wireless IC tag 1 comprised of the above with reference to FIG. 3. First, a ready-mixed concrete company prepares a lot of wireless IC tags 1 in an initial state, and in the manufacturing process of cement products to which cement, aggregate including gravels and water are kneaded, mixes them into the cement products, for example about 1 wireless IC tag per cubic meter of the cement product. Then an automatic measuring device arranged in a measuring process of cement products measures the characteristic value of the products including the proportion of water to cement, cement admixture and the temperature of cement products, and an IC tag writer 7 coupled to the automatic measuring device automatically writes the characteristic value of the products measured by the automatic measuring device and the manufacturing information consisting of the dates of manufacture in the mixed wireless IC tag 1. Furthermore, the manufacturing information written in this IC tag 1 is recorded also in a central control server 8 which intensively controls the quality control system of concrete, and linkage of data is promoted.

The cement products in which this wireless IC tag 1 is mixed is loaded into an agitating truck 9, and a person in charge of transportation writes the transportation information including dates of transportation into the wireless IC tag 1 mixed into the cement products by an agitating truck with an IC tag writer 7 which is installed in a PDA (Personal Digital Assistant) and is set to communicate wirelessly with previously encrypted signals.

When this agitating truck 9 arrives at a construction field, a person in charge of the field using an IC tag writer 10 installed in a PDA also writes the acceptance information including the dates of acceptance, the test results and the check of mixing into a wireless IC tag 1 with encrypted signals, and at the same time also records said information in a central control server 8. Then the cement products into which this wireless IC tag 1 is mixed are cast and a concrete structure is formed. General contractors in charge of the construction in the field can add records of the information on structures including bar arrangement, as needed, to the wireless IC tag 1 located in each construction zone or in each site with an IC tag writer 10.

After the concrete structure has been completed in this way, by using an IC tag reader 11 incorporated in a PDA which is set to communicate wirelessly with previously encrypted signals, various kinds of information recorded in a wireless IC tag 1 in the concrete structure can be read out.

The above-mentioned central control server 7 controls the information written into a wireless IC tag 1 in many construction fields, and provides, if needed, builders, clients of construction, users and various industry groups with said information.

In addition, described in the above-mentioned example was FeRAM of nonvolatile memory using ferroelectric substance as one example of a memory device used in this example, but it is not limited only to this, but a memory device with a nonvolatile function consisting of semiconducting materials will do.

In the above-mentioned configuration, a concrete quality control system using a wireless IC tag contained in a process of manufacturing cement products kneaded with cement, aggregate, and water, the wireless IC tag having an antenna section which is writable and readable of information through wireless communication, wherein a product characteristic value of the cement product is measured by an automatic measuring device arranged in the process of measuring this cement product, manufacturing information such as product characteristic value and the manufacturing date measured by said automatic measuring device is automatically written by an IC tag writer coupled with the automatic measuring device, and the data recorded in said wireless IC tag inside the structure can be read by an IC tag reader after said cement products are cast in the construction site and finished into a structure. Therefore, there is no possibility that the measured value is falsified by an automatic measuring device during manufacturing cement products, and the value is recorded as it is in the wireless IC tag and not only the reliability of the information increases but also there is no possibility of damage or loss of the wireless IC tag cast together with cement products and arranged in a structure and it possesses high reliability. As the information recorded in the wireless IC tag can be read at any time by the IC tag reader, it is reliable and expedient.

As the wireless IC tag has a solid form including a sphere, an ellipsoid or a polyhedron, it can also resist an applied force during kneading with cement, aggregate and water or an applied compression force during casting, and there is no possibility of damage or deterioration.

With a curved surface of the antenna section, it also becomes easier to communicate wirelessly with a wider directivity compared with a planate antenna.

As the antenna section with a curved surface is formed having a curved surface following said solid form of the wireless IC tag with a solid form including a sphere, an ellipsoid or a polyhedron, the wireless IC tag with a wider directivity of the antenna and easy to communicate wirelessly can also resist an applied force during kneading with cement, aggregate and water or an applied compression force during casting, and there is no possibility of damage or deterioration.

By communicating wirelessly with the signals encrypted between the IC tag writer and the IC tag reader, the wireless IC tag can also control the information securely as it is impossible to write or read except by predetermined devices.

Though EEPROM as a wireless IC tag is generally known as a nonvolatile memory device, the feature of the present invention is to be able to use the wireless IC tag semipermanently without battery exhaustion by equipping a power section which generates electricity by resonating the received waves without having a battery built-in using memory called FeRAM instead of EEPROM, and to be able to read and write at a higher speed and make it easier to use with low-voltage driving and little power consumption.

By making the size and specific gravity about the same as those of the aggregate kneaded into the cement product together, the wireless IC tag is mixed into the cement products dispersedly without unevenness during kneading of the cement products.

In addition, as there is no possibility of the wireless IC tag equipped with an antenna section being destroyed or damaged during kneading cement products because of the coating on the outer circumference, the wireless IC tag possesses higher reliability and is used stably.

What is claimed is:

1. A concrete quality control system using a wireless IC tag kneaded with cement, aggregate, and water, the system comprising:
   a cement product including cement, aggregate, and water kneaded together;
   a wireless IC tag contained in the cement product, the wireless IC tag having an antenna section, a nonvolatile memory device, and a power section, the wireless IC tag being configured such that information is writable thereon and readable therefrom by wireless communication through the antenna section;

a measuring device measuring manufacturing information of the cement product;

an IC tag writer coupled to the measuring device, the IC tag writer writing the manufacturing information to the wireless IC tag; and an IC tag reader reading the manufacturing information from the wireless IC tag, wherein the power section generates electricity without a battery by resonating with received radio waves, wherein the cement product with the wireless IC tag contained therein is usable to construct a structure, and the manufacturing information in the wireless IC tag is readable from the wireless IC tag inside the structure by the IC tag reader after the cement product is cast at a construction site and finished into the structure, wherein the wireless IC tag has a solid form shaped as one of a sphere, an ellipsoid, and a polyhedron, and wherein a size and specific gravity of the wireless IC tag are approximately the same as a size and specific gravity of the aggregate kneaded into the cement product such that the wireless IC tag can be dispersed into the cement product evenly during kneading of the cement product.

2. The quality control system according to claim 1, wherein the antenna section has a curved surface.

3. The quality control system according to claim 1, wherein the antenna has a curved surface following the solid form of the wireless IC tag.

4. The quality control system according to claim 1, wherein the wireless IC tag communicates wirelessly with the IC tag writer and the IC tag reader through encrypted signals.

5. The quality control system according to claim 1, wherein the nonvolatile memory device of the wireless IC tag is formed of semiconducting materials.

6. The quality control system according to claim 1, wherein the size and specific gravity of the wireless IC tag are the same as the size and specific gravity of the aggregate kneaded into the cement product such that the wireless IC tag can be dispersed into the cement product evenly during kneading of the cement product.

7. The quality control system according to claim 1, wherein an outer circumference of the wireless IC tag is covered with coating.

8. The quality control system according to claim 3, wherein the wireless IC tag communicates wirelessly with the IC tag writer and the IC tag reader through encrypted signals.

9. The quality control system according to claim 3, wherein the nonvolatile memory device of the wireless IC tag is formed of semiconducting materials.

10. The quality control system according to claim 4, wherein the nonvolatile memory device of the wireless IC tag is formed of semiconducting materials.

11. The quality control system according to claim 3, wherein the size and specific gravity of the wireless IC tag are the same as the size as a size and specific gravity of the aggregate kneaded into the cement product such that the wireless IC tag can be dispersed into the cement product evenly during kneading of the cement product.

12. The quality control system according to claim 4, wherein the size and specific gravity of the wireless IC tag are the same as the size and specific gravity of the aggregate kneaded into the cement product such that the wireless IC tag can be dispersed into the cement product evenly during kneading of the cement product.

13. The quality control system according to claim 5, wherein the size and specific gravity of the wireless IC tag are the same as the size and specific gravity of the aggregate kneaded into the cement product such that the wireless IC tag can be dispersed into the cement product evenly during kneading of the cement product.

14. The quality control system according to claim 3, wherein an outer circumference of the wireless IC tag is covered with coating.

15. The quality control system according to claim 4, wherein an outer circumference of the wireless IC tag is covered with coating.

16. The quality control system according to claim 5, wherein an outer circumference of the wireless IC tag is covered with coating.

17. The quality control system according to claim 6, wherein an outer circumference of the wireless IC tag is covered with coating.

18. A concrete quality control system using a wireless IC tag kneaded with cement, aggregate, and water, the system comprising:

a cement product including cement, aggregate, and water kneaded together; and a wireless IC tag contained in the cement product, the wireless IC tag having an antenna section, a nonvolatile memory device, and a power section, the wireless IC tag being configured such that information is writable thereon and readable therefrom by wireless communication through the antenna section, wherein the power section generates electricity without a battery by resonating with received radio waves, wherein the wireless IC tag is operable to record manufacturing information of the cement product from an IC tag writer which writes the manufacturing information to the wireless IC tag such that the manufacturing information can be read by an IC tag reader, and wherein the cement product with the wireless IC tag contained therein can be used to construct a structure, wherein the manufacturing information in the wireless IC tag can be read from the wireless IC tag inside the structure by the IC tag reader after the cement product is cast at a construction site and finished into the structure, wherein the wireless IC tag has a solid form shaped as one of a sphere, an ellipsoid, and a polyhedron, and wherein a size and specific gravity of the wireless IC tag are approximately the same as a size and specific gravity of the aggregate kneaded into the cement product such that the wireless IC tag can be dispersed into the cement product evenly during kneading of the cement product.

19. The quality control system according to claim 18, wherein the antenna section has a curved surface.

20. The quality control system according to claim 18, wherein the antenna has a curved surface following the solid form of the wireless IC tag.

21. The quality control system according to claim 18, wherein the wireless IC tag communicates wirelessly with the IC tag writer and the IC tag reader through encrypted signals.

22. The quality control system according to claim 18, wherein the nonvolatile memory device of the wireless IC tag is formed of semiconducting materials.

23. The quality control system according to claim 18, wherein the size and specific gravity of the wireless IC tag are the same as the size and specific gravity of the aggregate kneaded into the cement product such that the wireless IC tag can be dispersed into the cement product evenly during kneading of the cement product.

24. The quality control system according to claim 18, wherein an outer circumference of the wireless IC tag is covered with coating.

25. The quality control system according to claim 20, wherein the wireless IC tag communicates wirelessly with the IC tag writer and the IC tag reader through encrypted signals.

26. The quality control system according to claim 20, wherein the nonvolatile memory device of the wireless IC tag is formed of semiconducting materials.

27. The quality control system according to claim 21, wherein the nonvolatile memory device of the wireless IC tag is formed of semiconducting materials.

28. The quality control system according to claim 20, wherein the size and specific gravity of the wireless IC tag are the same as the size and specific gravity of the aggregate kneaded into the cement product such that the wireless IC tag can be dispersed into the cement product evenly during kneading of the cement product.

29. The quality control system according to claim 21, wherein the size and specific gravity of the wireless IC tag are the same as the size and specific gravity of the aggregate kneaded into the cement product such that the wireless IC tag can be dispersed into the cement product evenly during kneading of the cement product.

30. The quality control system according to claim 22, wherein the size and specific gravity of the wireless IC tag are the same as the size and specific gravity of the aggregate kneaded into the cement product such that the wireless IC tag can be dispersed into the cement product evenly during kneading of the cement product.

31. The quality control system according to claim 20, wherein an outer circumference of the wireless IC tag is covered with coating.

32. The quality control system according to claim 21, wherein an outer circumference of the wireless IC tag is covered with coating.

33. The quality control system according to claim 22, wherein an outer circumference of the wireless IC tag is covered with coating.

34. The quality control system according to claim 23, wherein an outer circumference of the wireless IC tag is covered with coating.

* * * * *